US010576176B2

(12) United States Patent
Higashiyama et al.

(10) Patent No.: US 10,576,176 B2
(45) Date of Patent: Mar. 3, 2020

(54) STERILIZING SYSTEM

(71) Applicant: SUNTORY HOLDINGS LIMITED, Osaka (JP)

(72) Inventors: Kenichi Higashiyama, Kyoto (JP); Kenta Tominaga, Kyoto (JP); Yuji Hirayama, Kyoto (JP); Kazuki Yoshihara, Kyoto (JP); Toshiaki Iizuka, Tokyo (JP); Satoshi Moriya, Tokyo (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 15/767,904

(22) PCT Filed: Oct. 12, 2016

(86) PCT No.: PCT/JP2016/080264
§ 371 (c)(1),
(2) Date: Apr. 12, 2018

(87) PCT Pub. No.: WO2017/065179
PCT Pub. Date: Apr. 20, 2017

(65) Prior Publication Data
US 2018/0296715 A1    Oct. 18, 2018

(30) Foreign Application Priority Data
Oct. 13, 2015    (JP) .................................. 2015-202176

(51) Int. Cl.
*A61L 2/14*    (2006.01)
*A61L 2/20*    (2006.01)
(Continued)

(52) U.S. Cl.
CPC .............. *A61L 2/14* (2013.01); *A61B 18/042* (2013.01); *A61L 2/0011* (2013.01); *A61L 2/20* (2013.01);
(Continued)

(58) Field of Classification Search
CPC . A61L 2/14; A61L 2/20; A61L 2/0011; A61B 18/042
See application file for complete search history.

(56) References Cited

U.S. PATENT DOCUMENTS 8,900,521 B2    12/2014   Hancock
2010/0247403 A1    9/2010   Hancock
(Continued)

FOREIGN PATENT DOCUMENTS

GB    2458329    9/2009
JP    10-129627    5/1998
(Continued)

OTHER PUBLICATIONS

International Search Report issued in Patent Application No. PCT/JP2016/080264 and English Translation, dated Nov. 15, 2016.
(Continued)

*Primary Examiner* — Sean E Conley
(74) *Attorney, Agent, or Firm* — Greenblum & Bernstein, P.L.C.

(57) ABSTRACT

In a sterilizing system, a sterilizing device receives supply of oxygen and steam. The sterilizing device produces oxygen plasma containing ozone from the supplied oxygen and discharges the produced oxygen plasma and reactive oxygen produced through reaction between the supplied steam and the oxygen plasma as a sterilizing agent. And, the sterilizing system includes an ozone collecting unit for collecting ozone contained in the discharged oxygen plasma.

8 Claims, 3 Drawing Sheets

(51) Int. Cl.
*A61B 18/04* (2006.01)
*A61L 2/00* (2006.01)
(52) U.S. Cl.
CPC ........ *A61L 2202/11* (2013.01); *A61L 2202/14* (2013.01)

(56) References Cited

U.S. PATENT DOCUMENTS

| | | |
|---|---|---|
| 2010/0296977 A1 | 11/2010 | Hancock |
| 2013/0142694 A1 | 6/2013 | Krohmann et al. |
| 2015/0056107 A1 | 2/2015 | Hancock |

FOREIGN PATENT DOCUMENTS

| | | |
|---|---|---|
| JP | 2013-28398 | 2/2013 |
| WO | 2005/023319 | 3/2005 |

OTHER PUBLICATIONS

Written Opinion issued in Patent Application No. PCT/JP2016/080264, dated Nov. 15, 2016.
International Preliminary Report on Patentability for PCT/JP2016/080264, dated Apr. 17, 2018 and English language translation thereof.
Official Communication issued in European Patent Office (EPO) Patent Application No. 16855432.7, dated Jun. 3, 2019.

STERILIZING SYSTEM

TECHNICAL FIELD

This disclosure relates to a sterilizing system configured to sterilize a sterilization-subject article such as a cap of a container.

RELATED ART

As a method of sterilizing a cap of a container such as a PET bottle as one example of a sterilization-subject article, there is known a sterilizing method disclosed in Japanese Unexamined Patent Application Publication No. 2013-28398 (Patent Document 1). Patent Document 1 discloses a method of effecting sterilization of an inside of the container by discharging a sterilizing agent containing hydrogen peroxide into the bottle or its cap.

In the case of employing a sterilizing agent containing hydrogen peroxide as implemented in the technique of Patent Document 1, it is necessary to effect cleaning subsequently in order not to allow the sterilizing agent to remain in the cap. However, removal of sterilizing agent entirely by means of cleaning is difficult, so there is a risk of the sterilizing agent remaining in the cap. Moreover, with the sterilizing method of Patent Document 1, a sterilizing agent spraying operation and the cleaning operation subsequent thereto are carried out at a high temperature. Thus, in the case of a cap of a PET bottle formed of resin material suffering from thermal contraction, various restrictions will be imposed on its sterilizing process in order to avoid excessive thermal contraction or deformation.

Patent Document 1: Japanese Unexamined Patent Application Publication No. 2013-28398

SUMMARY

Problem to be Solved by Invention

To cope with the above, the present inventors have discovered a novel method according to which a sterilizing device configured to sterilize a sterilization-subject article without risks of remaining of sterilizing agent on the sterilization-subject article such as a cap to be fitted on a bottle, etc. is used to generate plasma and reactive oxygen produced by reacting the plasma with steam and the plasma are used for effecting sterilization. Reactive oxygen dies out over time, so it will not remain. Moreover, sterilization using reactive oxygen does not require application of such heat which may cause thermal contraction of the sterilization-subject article. Therefore, by using this method that effects sterilization with a sterilizing agent containing plasma and reactive oxygen, it is possible to avoid residual of the sterilizing agent on the sterilization-subject article and occurrence of excessive thermal contraction/deformation of the sterilization-subject article. However, since this method is novel, sufficient contemplation has not yet been made, respecting an efficient operation of a sterilization system using this method.

Thus, there remains a need for realizing a sterilization system capable of effecting sterilization using reactive oxygen in an efficient manner.

Solution

A sterilizing system relating to the present invention is a sterilization system including a sterilizing device configured to generate plasma and to effect sterilization of a sterilization-subject article with the generated plasma, wherein:

the sterilizing device receives supply of oxygen and steam (vapor);

the sterilizing device is configured such that as the plasma, oxygen plasma containing ozone is produced from the supplied oxygen, and the produced oxygen plasma and reactive oxygen produced through reaction between the supplied steam and the oxygen plasma are discharged together as sterilizing agent; and an ozone collecting unit is provided for collecting the ozone contained in the discharged oxygen plasma and returning this ozone to the sterilizing device.

Referring further to the above arrangement, in the sterilizing device, oxygen ($O_2$) is supplied and this oxygen is converted into plasma, whereby oxygen plasma containing oxygen radical and ozone ($O_3$) is produced. Then, as this is reacted with steam, reactive oxygen is produced. In particular, through the reaction between oxygen plasma and steam, there is mainly produced hydroxy radical (.OH) which has a particularly high reactivity among reactive oxygen species.

More specifically, with the reaction between steam and plasma, hydrogen radical (.H) and hydroxy radical are produced as shown by Formula (1) below.

$$H_2O \rightarrow .H + .OH \quad (1)$$

Also, the hydrogen radical reacts with the ozone to produce hydroxy radical and oxygen ($O_2$) as shown by Formula (2) below.

$$.H + O_3 \rightarrow .OH + O_2 \quad (2)$$

Formula (1) and Formula (2) can be combined into Formula (3) below.

$$H_2O + O_3 \rightarrow 2.OH + O_2 \quad (3)$$

Namely, with the reaction between oxygen plasma and steam, the reaction according to Formula (3) is caused to take place, whereby hydroxy radical (.OH) can be produced in an efficient manner. As a result, the reactive oxygen thus produced contains mainly hydroxy radical. In this way, with the reaction between ozone and $H_2O$, it will contain mainly such hydroxy radical having particularly high reactivity, so a high sterilization effect can be achieved.

However, not all ozone is necessarily reacted with $H_2O$, but some ozone will be discharged from the sterilizing device as oxygen plasma unreacted with steam. Then, according to the above-described arrangement, there is provided an ozone collecting unit for collecting the ozone contained in the discharged oxygen plasma and returning this ozone to the sterilizing device. With this arrangement, ozone can be reused for production of hydroxy radical, so an operation without loss of ozone becomes possible. Accordingly, the sterilization using reactive oxygen can be effected in an efficient manner.

Next, preferred embodiments of the sterilizing system relating to the present invention will be explained. It is understood, however, that the scope of the present invention is not limited by these preferred embodiments described below.

According to one preferred embodiment, the ozone collected by the ozone collecting unit is supplied to the sterilizing device together with the oxygen.

With the above arrangement, since the collected ozone is returned to the sterilizing device together with the supplied oxygen, the system configuration can be made more simple than a configuration of returning the ozone into the sterilizing device from a different portion than oxygen and steam.

According to one preferred embodiment, the ozone collected by the ozone collecting unit is supplied to the sterilizing device together with the steam.

With the above arrangement, since the collected ozone is returned to the sterilizing device together with the supplied steam, the system configuration can be made more simple than a configuration of returning the ozone into the sterilizing device from a different portion than oxygen and steam.

According to one preferred embodiment, there is provided a dehumidifying unit for dehumidifying the ozone collected by the ozone collecting unit.

In case steam is contained in the ozone gas collected by the ozone collecting unit, if ozone containing the steam is returned to a plasma producing unit, this plasma producing unit may malfunction due to the steam. To cope with this, according to the above-described arrangement, there is provided a dehumidifying unit for dehumidifying the collected ozone. As a result, ozone can be reused in a manner safe for the radical oxygen production.

According to one preferred embodiment, there are provided an ozone meter for determining an amount of the ozone collected by the ozone collecting unit and a supplied oxygen controlling unit for adjusting an amount of the oxygen to be supplied to the sterilizing device based on the amount of ozone determined by the ozone meter.

In case ozone is to be reused, even if an amount of oxygen to be supplied is reduced by an amount corresponding thereto, it is still possible to produce a same amount of radical oxygen. In this respect, with the above-described arrangement, it becomes possible to adjust the amount of oxygen to be supplied by the amount of ozone reduced, thus making it possible to reduce the amount of oxygen used. Consequently, the sterilization using reactive oxygen can be effected in an even more efficient manner.

EMBODIMENTS

[First Embodiment]

Next, an embodiment of a sterilizing system relating to the present invention will be explained with reference to the accompanying drawings. A sterilizing system 100 according to the instant embodiment is provided for sterilizing, as an example of a sterilization-subject article, a cap 80 of a container such as a PET bottle. And, the sterilizing system 100 includes a sterilizing device 1 configured to generate plasma and to sterilize the cap 80 by the obtained plasma. The sterilizing device 1 receives supply of oxygen and steam. The sterilizing device 1 produces oxygen plasma containing ozone from the supplied oxygen and discharges a sterilizing agent containing the produced plasma and reactive oxygen (reactive oxidizing species (ROS), e.g. OH radical or singlet oxygen, etc.) produced from a reaction between the supplied steam and the produced plasma, thus sterilizing the cap 80. Then, firstly, there will be explained the device configuration of the sterilizing device 1 for effecting sterilization using reactive oxygen.

Figure 1:
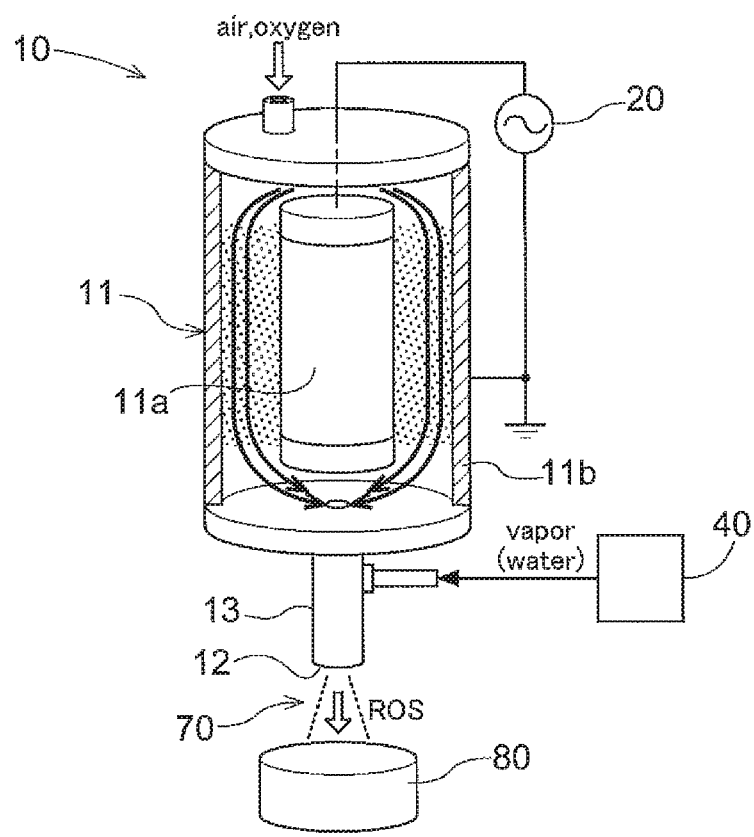
FIG. 1 is a schematic configuration diagram of a sterilizing device for effecting sterilization using reactive oxygen.
Figure 4:
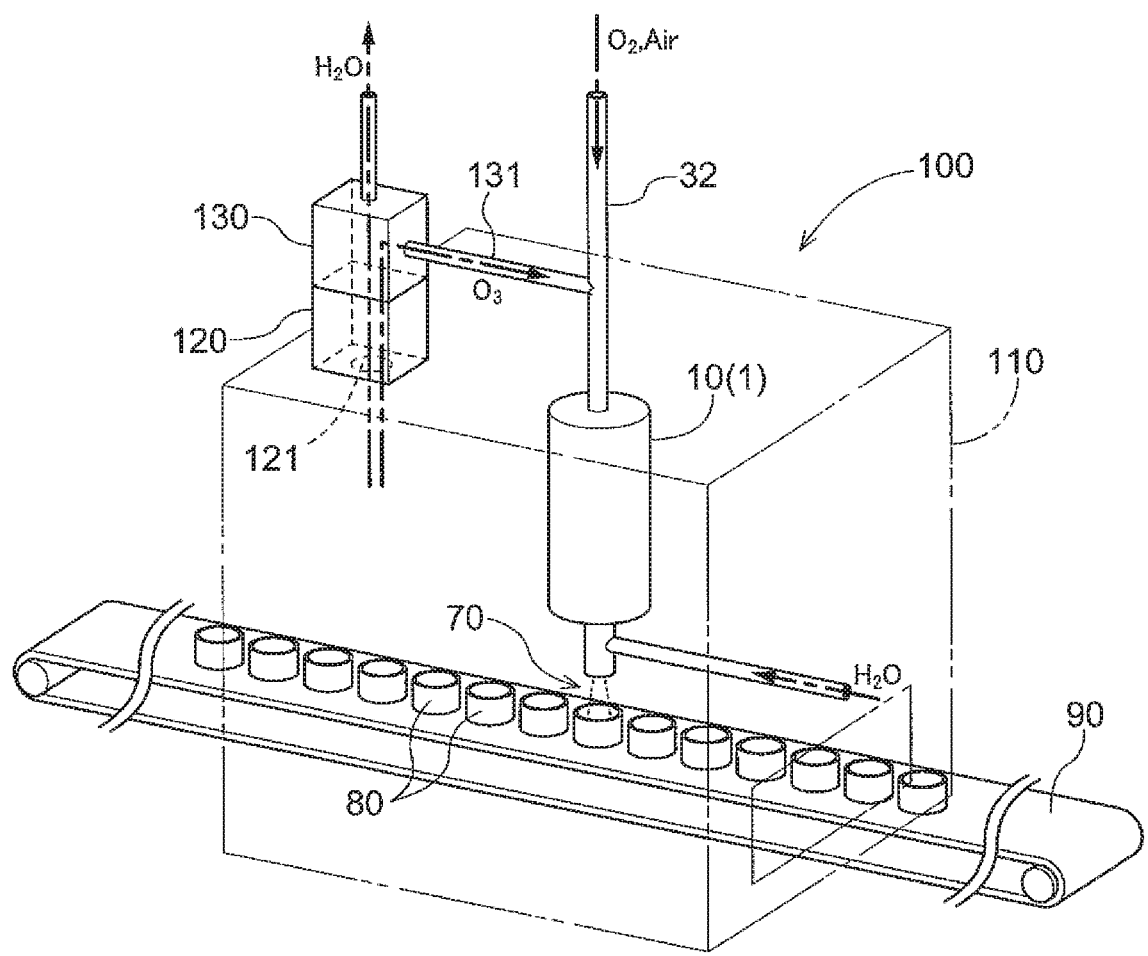
FIG. 4 is a view showing a sterilizing system according to a first embodiment.
Figure 5:
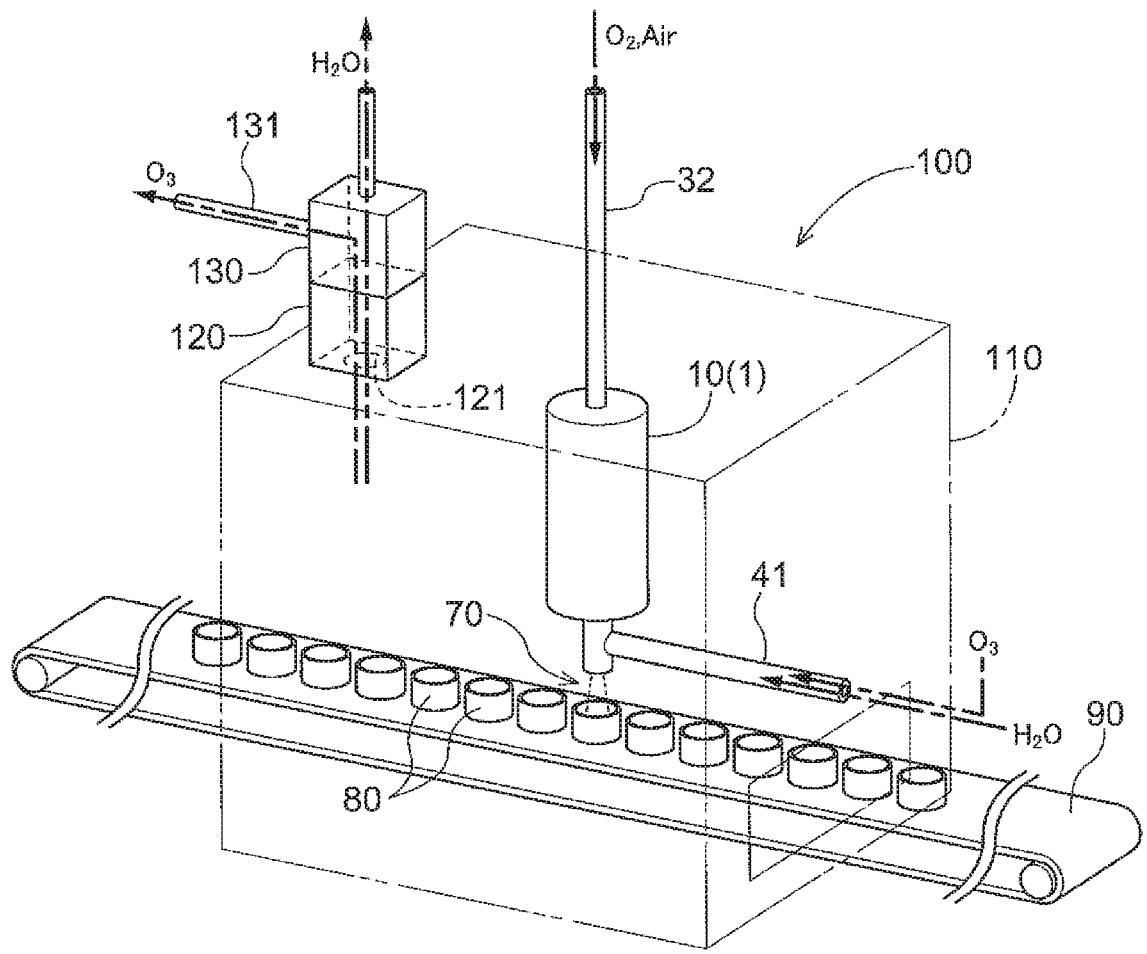
FIG. 5 is a view showing a sterilizing system according to a second embodiment.

FIG. 1 shows a production mechanism for reactive oxygen in the sterilizing device 1. The sterilizing device 1 incudes a nozzle 10 configured to produce reactive oxygen and discharge (irradiate) sterilizing agent 70 containing the reactive oxygen to the cap 80. This nozzle 10 includes a plasma producing unit 11 for producing plasma, an outlet 12 for discharging the sterilizing agent 70 containing the plasma and the reactive oxygen, and a relaying section 13 between the plasma producing unit 11 and the outlet 12. Incidentally, FIGS. 1, 4 and 5 show a configuration in which the sterilizing device 1 discharges the sterilizing agent 70 containing reactive oxygen directly to the cap 80. However, the invention is not limited thereto. As an alternative, instead of directly discharging the sterilizing agent 70 to the cap 80, an indirect sterilization of the cap 80 may be implemented, e.g. by discharging the sterilizing agent 70 into a chamber through which the cap 80 is passed so that this cap 80 may be sterilized by an amount of the sterilizing agent 70 filled in the chamber.

This nozzle 10 produces so-called atmospheric pressure plasma within the device. By using the atmospheric pressure plasma, e.g. a vacuum vessel required for producing low pressure plasma can be omitted, so that the device cost can be reduced. Further, as the production process is continuous, the work efficiency is high. Moreover, since the production is possible even at a low temperature, there is obtained a further advantage of not needing to expose the process-subject article to a high temperature. Next, the production of such high atmospheric pressure plasma (to be referred to simply as "plasma" hereinafter) and production of reactive oxygen using plasma will be explained.

The plasma producing unit 11 has a well-known construct including an internal electrode 11a and an external electrode 11b. In the plasma producing unit 11, by an AC power source 20, a high voltage (e.g. effective voltage of 20 kV at frequency of 14 kHz) is applied between the internal electrode 11a and the external electrode 11b, whereby an electric field is generated within the plasma producing unit 11. And, into the plasma producing unit 11, gas together with air is fed to pass this gas through the generated electric field, thus producing plasma. The produced plasma is then sent to the relaying section 13. In the instant embodiment, into the plasma producing unit 11, oxygen ($O_2$) is supplied as an example of "gas", so that ozone-containing plasma is produced as "plasma" inside the plasma producing unit 11. More particularly, by the plasma production process, oxygen radical and ozone ($O_3$) are generated, which are then sent to the relaying section 13.

The relaying section 13 is connected to an evaporator 40 and steam is also sent to the relaying section 13. Within the relaying section 13, the plasma (oxygen radical and ozone) sent from the plasma producing unit 11 and the steam (vapor) sent from the evaporator 40 react with each other, thus producing reactive oxygen. In the instant embodiment, an arrangement is provided such that as the oxygen plasma (oxygen radical and ozone) and the steam are caused to react with each other, there is mainly produced hydroxy radical (.OH) which has a particularly high reactivity among reactive oxygen species.

More specifically, with the reaction between steam and plasma, hydrogen radical (.H) and hydroxy radical are produced as shown by Formula (4) below.

$$H_2O \rightarrow .H + .OH \tag{4}$$

Also, the hydrogen radical reacts with the ozone to produce hydroxy radical and oxygen ($O_2$) as shown by Formula (5) below.

$$.H+O_3 \rightarrow .OH+O_2 \quad (5)$$

Formula (4) and Formula (5) can be combined into Formula (6) below.

$$H_2O+O_3 \rightarrow 2.OH+O_2 \quad (6)$$

Namely, with the reaction between oxygen plasma and steam, the reaction according to Formula (6) is caused to take place, whereby hydroxy radical (.OH) can be produced in an efficient manner. As a result, the reactive oxygen thus produced contains mainly hydroxy radical having such particularly high reactivity. And, as it contains mainly such hydroxy radical having particularly high reactivity, a high sterilization effect can be achieved. And, such produced reactive oxygen, steam and unreacted plasma (oxygen radical and ozone) will be discharged together as the sterilizing agent 70 through the outlet 12 to the cap 80, whereby the cap 80 is sterilized.

Figure 2:
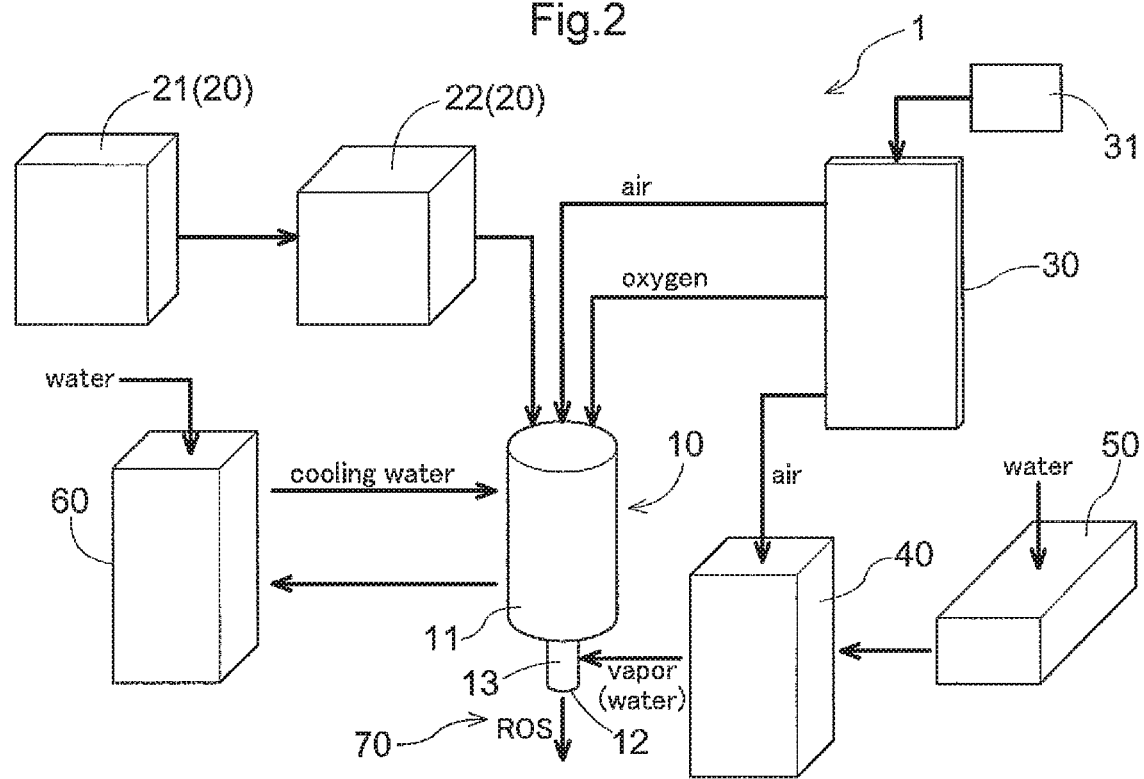
FIG. 2 is a schematic configuration block diagram of the sterilizing device for effecting sterilization using reactive oxygen.

Next, a device configuration shown in FIG. 2 of the sterilizing device 1 for effecting sterilization using reactive oxygen will be explained. The sterilizing device 1 includes, in addition to the nozzle 10, a generator 21 and a transformer 22 which together constitute the AC power source 20, a gas supplying unit 30 for feeding various kinds of gas to the nozzle 10 and to an evaporator 40, the evaporator 40 for feeding steam to the relaying section 13, a pump 50 for feeding water to the evaporator 40, and a chiller 60 for feeding cold water to the nozzle 10.

The generator 21 generates an alternating current. For instance, in this embodiment, there is employed one having a frequency of 14 kHz, an effective voltage of 300 V and an effective current of 11A. Then, the alternating current supplied by the generator 21 is boosted from 300 V to 20 kV by the transformer 22. With this, a high voltage of 20 kV is applied between the internal electrode 11$a$ and the external electrode 11$b$ in the plasma producing unit 11.

The gas supplying unit 30 is connected to the plasma producing unit 11 and supplies oxygen ($O_2$) together with air to the nozzle 10 (plasma producing unit 11) and also supplies air to the evaporator 40 for feeding the steam produced by the evaporator 40 to the relaying section 13. The gas supplying unit 30 includes a control panel 31. By operating this control panel 31, a supplying amount of the various gases to the respective components can be controlled. In this embodiment, by operating the control panel 31, for instance, air at 6 L/min and oxygen at 3 L/min can be respectively sent to the nozzle 10 and air at 3 L/min can be sent to the evaporator 40.

The evaporator 40 is connected to the relaying section 13 and feeds steam to this relaying section 13. The evaporator 40 is arranged such that an electric heating wire incorporated therein (not shown) is heated to 300° C., thus heating water supplied from the pump 50 with this heated wire to generate steam and as this steam is mixed with the air supplied from the gas supplying unit 30, the steam together with the air will be supplied to the relaying section 13. Incidentally, in this embodiment, the pump 50 is configured to supply water at 1.2 mL/min to the evaporator 40.

The chiller 60 is configured to cool the nozzle 10 by supplying cold water thereto, which nozzle 10 has been heated with the application of the high voltage.

In operation with the sterilizing device 1 configured as described above, oxygen supplied together with air from the gas supplying unit 30 to the nozzle 10 is converted into plasma at the plasma producing unit 11 and at the relaying section 13, resultantly produced oxygen plasma is reacted with the steam supplied from the evaporator 40 together with air, thus continuously producing reactive oxygen containing hydroxy radical as the main component thereof. Then, the reactive oxygen, steam and unreacted plasma produced continuously at the relaying section 13 will be discharged as the sterilizing agent 70 continuously via the outlet 12, thus enabling continuous treatment of the caps 80. In this embodiment, for instance, sterilizing agent 70 containing plasma and the reactive oxygen will be discharged via the outlet at a flow rate of 50000 mm/sec at a temperature ranging from 50 to 80° C.

Effecting sterilization with using reactive oxygen provides the following advantages. If a sterilizing agent containing hydrogen peroxide is used, it is necessary to effect a cleaning operation thereafter so that the sterilizing agent will not remain on the sterilization-subject article. However, elimination of all sterilizing agent by cleaning is difficult, so there is a risk of some sterilizing agent remaining on the sterilization-subject article. Also, since spraying of the sterilizing agent and the cleaning subsequent thereto are effected at a high temperature, if the sterilization-subject article is made of a material such as a resin which suffers thermal contraction, the sterilization process will be subjected to various limitations in order to prevent excessive thermal contraction or deformation. On the other hand, reactive oxygen dies out over time, so it will not remain. Moreover, sterilization using reactive oxygen does not require application of such heat which may cause thermal contraction of the sterilization-subject article. Therefore, it is possible to avoid residual of the sterilizing agent on the sterilization-subject article and occurrence of excessive thermal contraction/deformation of the sterilization-subject article.

In the above, the system configuration for sterilization using reactive oxygen has been described. In the sterilizing system 100 according to the instant embodiment, for more efficient operation, the system is configured such that ozone produced in the plasma producing unit 11 and discharged as unreacted plasma via the outlet 12 is collected and returned to the sterilizing device 1 for reuse. Namely, as described above, ozone is utilized for production of hydroxy radical and unreacted ozone discharged via the outlet 12 is returned to the sterilizing device 1 to be reused for hydroxy radical production, thus realizing efficient operation without loss of ozone. Next, its configuration will be explained with reference to e.g. FIGS. 3 and 4.

Figure 3:
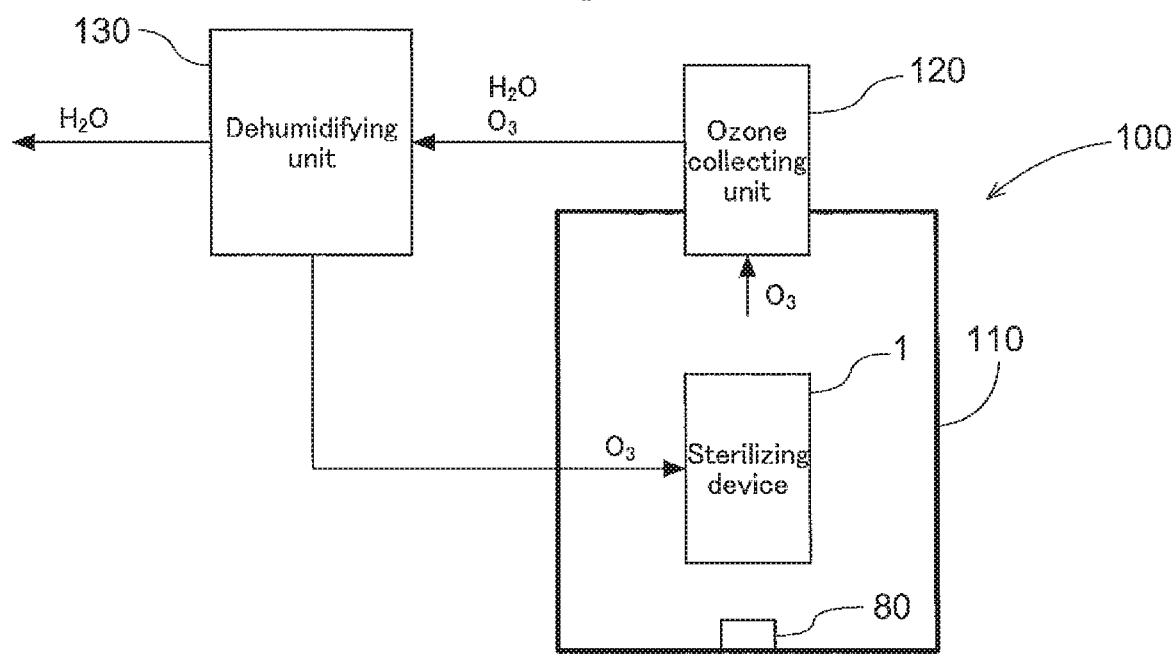
FIG. 3 is a schematic configuration diagram of a sterilizing system.

FIG. 3 shows a schematic configuration of the sterilizing system 100 relating to the instant embodiment. The sterilizing system 100 relating to the instant embodiment includes an ozone collecting unit 120 for collecting ozone contained in the oxygen plasma discharged via the outlet 12. More particularly, the sterilizing device 1 is configured such that the sterilization of the cap 80 is effected inside a chamber 110 and the chamber 110 includes an ozone collecting unit 120. And, in the sterilizing system 100 relating to this embodiment, there is provided a dehumidifying unit 130 for dehumidifying ozone collected by the ozone collecting unit 120. Thus, ozone dehumidified by the dehumidifying unit 130 is returned to the sterilizing device 1 to be reused for the hydroxy radical production.

Incidentally, the ozone collecting unit 120 is not particularly limited as long as it can collect ozone. For instance, it can be configured to selectively collect ozone alone with use of a filter. Or, e.g. it can be configured to collect gas containing ozone inside the chamber 110 by a suction fan or the like. Further, the dehumidifying unit 130 too is not particularly limited as long as it can dehumidify ozone gas. Dehumidification can be carried out by any known appropriate method.

FIG. 4 shows the specific configuration of the sterilizing system 100 relating to the instant embodiment (incidentally, in FIG. 4, illustration of the other arrangements of the sterilizing device 1 other than that of the nozzle 10 is omitted.) As shown in FIG. 4, in this embodiment, ozone collected by the ozone collecting unit 120 is supplied to the plasma producing unit 11 together with the oxygen supplied from the gas supplying unit 30. More particularly, the nozzle 10 is disposed inside the chamber 110 and the cap 80 conveyed by a conveying unit 90 such as a conveyer is sterilized inside the chamber 110. The chamber 110 includes the ozone collecting unit 120 and introduces ozone together with gas present inside the chamber 110 via a suction inlet 121. And, upwardly of the ozone collecting unit 120, the dehumidifying unit 130 is provided continuously. This dehumidifying unit 130 dehumidifies (i.e. separates $H_2O$) the ozone gas collected by the ozone collecting unit 120. A conductive passage 131 for the ozone gas after being dehumidified by the dehumidifying unit 130 is connected to an oxygen supplying passage 32 for supplying oxygen from the gas supplying unit 30. With this arrangement, together with oxygen ($O_2$) supplied via the air from the gas supplying unit 30, the dehumidified ozone gas ($O_3$) collected by the ozone collecting unit 120 is supplied to the plasma producing unit 11. And, the ozone collected by the ozone collecting unit 120 is also supplied to the relaying section 13 to be reused for the hydroxy radical production through the reaction with steam ($H_2O$). In this way, ozone can be utilized without loss, so the sterilization using reaction oxygen can be effected in an even more efficient manner.

Further, if ozone containing steam is returned to the plasma producing unit 11, the steam may cause a trouble in the plasma producing unit 11. In this, ozone gas dehumidified by the dehumidifying unit 130 can be reused in a safe manner for the reactive oxygen production.

[Second Embodiment]

A second embodiment of the sterilizing system relating to the present invention will be explained with reference to the accompanying drawings. In this embodiment, the destination of ozone gas collected by the ozone collecting unit 120 differs from the first embodiment. Next, the sterilizing system relating to this embodiment will be explained, respecting mainly its difference from the first embodiment. Incidentally, respecting those aspects not explicitly described, they are same as the first embodiment and denoted with the same reference marks/numerals; and explanation thereof will be omitted.

In the sterilizing system 100 shown in FIG. 5 and relating to this embodiment, the conductive passage 131 for ozone gas after dehumidification by the dehumidifying unit 130 is connected to a steam supplying passage 41 for supplying steam from the evaporator 40 (incidentally, in FIG. 5, the connecting portion between the ozone gas conductive passage 131 and the steam supplying passage 41 is omitted from its illustration). With this, ozone ($O_3$) collected by the ozone collecting unit 120, together with the steam ($H_2O$) supplied from the evaporator, is supplied to the relaying section 13. And, the ozone collected by the ozone collecting unit 120 is also supplied to the relaying section 13 and this ozone too is reused in the hydroxy radical production through the reaction between oxygen plasma and the steam ($H_2O$) in the relaying section 13. In this way, as ozone is used without loss, the sterilization using reactive oxygen can be effected in an even more efficient manner.

Incidentally, in this embodiment, alternatively, with omission of the dehumidifying unit 130, the ozone gas collected by the ozone collecting unit 120 can be supplied, without dehumidification, directly to the steam supplying passage 41.

[Other Embodiments]

Lastly, other embodiments of the sterilizing system relating to the present invention will be explained. Incidentally, the arrangements/configurations to be disclosed in the following embodiments can be used in combination with the arrangements/configurations disclosed in the other embodiment's) in any desired manner, as long as no contraction occurs as a result of such combination.

(1) In the foregoing embodiment, the sterilizing system 100 may be provided with an ozone meter for determining an amount of the ozone collected by the ozone collecting unit 120 and a supplied oxygen controlling unit for adjusting an amount of the oxygen to be supplied by the gas supplying unit 30 based on the amount of ozone determined by the ozone meter. With this, it becomes possible to implement a mode of such operation wherein the amount of oxygen to be supplied by the gas supplying unit 30 is reduced by the amount of ozone returned to the sterilizing device 1. Consequently, the sterilization using reaction oxygen can be effected in an even more efficient manner.

(2) In the foregoing embodiment, there was disclosed an exemplary arrangement in which collected ozone is returned to the sterilizing device 1 together with oxygen or steam. However, the embodiment of the present invention is not limited thereto. For instance, by connecting the ozone gas conductive passage 131 not to the oxygen supplying passage 32 or the steam supplying passage 41, but directly to the sterilizing device 1, the collected ozone may be returned to the sterilizing device 1.

(3) In the foregoing embodiment, there was disclosed an exemplary arrangement in which the cap 80 is used as the sterilization-subject article. However, the embodiment of the present invention is not limited thereto. The choice of the sterilization-subject article can be made variably as desired.

(4) In the foregoing embodiment, there was disclosed an exemplary arrangement in which the nozzle 10 is provided inside the chamber 110 for discharging the sterilizing agent 70 directly to the cap 80. Alternatively, by providing the nozzle 10 outside the chamber 110 and also connecting the outlet 12 to the chamber 110, the sterilizing agent 70 may be discharged into the chamber 110 and the cap 80 may be sterilized indirectly by the amount of sterilizing agent 70 filled inside the chamber 110.

(5) Respecting the other arrangements/configurations too, the embodiments disclosed in this detailed description are only exemplary, and the scope of the present invention is not limited thereto. One skilled in the art will readily understand that other modifications will be made possible as needed or desired without departing from the essence of the present invention. Therefore, it is understood that such other variations and modified embodiments made without departing from the inventive essence are also intended be included in the scope of the present invention.

INDUSTRIAL APPLICABILITY

The present invention is applicable to a sterilizing system for sterilizing a sterilization-subject such as a cap.

DESCRIPTION OF REFERENCE MARKS/NUMERALS

1: sterilizing device
70: sterilizing agent
80: cap (sterilization-subject article)
100: sterilizing system
120: ozone collecting unit
130: dehumidifying unit

The invention claimed is:

1. A sterilizing system including a sterilizer configured to generate plasma and to effect sterilization of a sterilization-subject article with the generated plasma, wherein:
the sterilizer receives a supply of oxygen, via an oxygen supplying passage, and steam provided via a steam supplying passage that has a steam outlet in fluid communication with the oxygen supplying passage;
the sterilizer is configured such that an oxygen plasma containing ozone, provided as the plasma, is produced from the supplied oxygen, and the produced oxygen plasma and reactive oxygen produced through reaction between the supplied steam and the oxygen plasma are discharged, from an outlet of the sterilizer, together as sterilizing agent;
an enclosure surrounding the sterilizer to define a sterilization chamber that is configured to allow sterilization of the sterilization-subject article therein,
the sterilization chamber including an ozone collector in fluid communication with the outlet of the sterilizer so as to collect the ozone contained in the discharged oxygen plasma, and
a conductive passage connected to the ozone collector and in fluid communication with the oxygen supplying passage of the sterilizer so as to transfer the ozone contained in the discharged oxygen plasma and return the collected ozone to the sterilizer via the oxygen supplying passage,
wherein the conductive passage is positioned outside of the enclosure, and
wherein an outlet of the conductive passage is connected downstream of an inlet of the oxygen supplying passage and upstream of the steam outlet of the steam supplying passage.

2. The sterilizing system of claim 1, wherein the collected ozone is supplied to the sterilizer together with the oxygen.

3. The sterilizing system of claim 1, wherein the collected ozone is supplied to the sterilizer together with the steam.

4. The sterilizing system of claim 2, wherein there is provided a dehumidifier in fluid communication with the ozone collector so as to dehumidify the collected ozone.

5. The sterilizing system of claim 2, wherein there are provided an ozone meter for determining an amount of the ozone collected by the ozone collector and a supplied oxygen controller for adjusting an amount of the oxygen to be supplied to the sterilizer based on the amount of ozone determined by the ozone meter.

6. A sterilizing system including a sterilizer configured to generate plasma and to effect sterilization of a sterilization-subject article with the generated plasma, wherein:
the sterilizer receives supply of oxygen and steam;
the sterilizer is configured such that an oxygen plasma containing ozone, provided as the plasma, is produced from the supplied oxygen, and the produced oxygen plasma and reactive oxygen produced through reaction between the supplied steam and the oxygen plasma are discharged together as sterilizing agent; and
an ozone collector fluidly connected to the sterilizer and configured to collect the ozone contained in the discharged oxygen plasma and return the collected ozone to the sterilizer,
wherein the collect ozone is supplied to the sterilizer together with the oxygen, and
wherein there is provided a dehumidifier in fluid communication with the ozone collector so as to dehumidify the collected ozone.

7. The sterilizing system of claim 6, wherein the collected ozone is supplied to the sterilizer together with the steam.

8. The sterilizing system of 6, wherein there are provided an ozone meter for determining an amount of the ozone collected by the ozone collector and a supplied oxygen controller for adjusting an amount of the oxygen to be supplied to the sterilizer based on the amount of ozone determined by the ozone meter.

* * * * *